(12) United States Patent
Salzman

(10) Patent No.: US 9,079,002 B1
(45) Date of Patent: Jul. 14, 2015

(54) CERAMIC NANOCHANNEL DRUG DELIVERY DEVICE AND METHOD OF FORMATION

(71) Applicant: Texas Instruments Incorporated, Dallas, TX (US)

(72) Inventor: James Fred Salzman, Anna, TX (US)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 0 days.

(21) Appl. No.: 14/175,530

(22) Filed: Feb. 7, 2014

(51) Int. Cl.
| | |
|---|---|
| B23K 31/02 | (2006.01) |
| A61M 5/00 | (2006.01) |
| A61M 31/00 | (2006.01) |
| C04B 37/00 | (2006.01) |
| C04B 35/10 | (2006.01) |
| C04B 41/00 | (2006.01) |
| C04B 41/91 | (2006.01) |
| B23K 1/00 | (2006.01) |

(52) U.S. Cl.
CPC .............. *A61M 31/002* (2013.01); *C04B 35/10* (2013.01); *C04B 37/005* (2013.01); *C04B 37/006* (2013.01); *C04B 41/0036* (2013.01); *C04B 41/91* (2013.01); *B23K 1/00* (2013.01)

(58) Field of Classification Search
None
See application file for complete search history.

(56) References Cited

U.S. PATENT DOCUMENTS

| | | | | |
|---|---|---|---|---|
| 3,948,254 A | * | 4/1976 | Zaffaroni | 128/833 |
| 5,798,042 A | * | 8/1998 | Chu et al. | 210/490 |
| 5,985,328 A | * | 11/1999 | Chu et al. | 424/489 |
| 6,776,860 B2 | * | 8/2004 | Arai et al. | 156/89.11 |
| 8,071,156 B2 | * | 12/2011 | Weber et al. | 427/2.24 |
| 8,101,402 B2 | | 1/2012 | Holmes | |
| 8,187,255 B2 | * | 5/2012 | Weber et al. | 604/890.1 |
| 8,480,637 B2 | * | 7/2013 | Ferrari et al. | 604/264 |
| 2006/0180469 A1 | * | 8/2006 | Han et al. | 204/601 |
| 2007/0066138 A1 | * | 3/2007 | Ferrari et al. | 439/607 |
| 2009/0214392 A1 | * | 8/2009 | Kameoka et al. | 422/102 |
| 2009/0214622 A1 | * | 8/2009 | Poinern et al. | 424/443 |
| 2015/0032088 A1 | * | 1/2015 | Grattoni et al. | 604/522 |

OTHER PUBLICATIONS

Seung Ho Lee, et al., "Microchip for Sustained Drug Delivery by Diffusion Through Microchannels", AAPS PharmSciTech, vol. 13, No. 1, Mar. 2012, pp. 211-217.

* cited by examiner

*Primary Examiner* — Kiley Stoner
(74) *Attorney, Agent, or Firm* — Alan A. R. Cooper; Frank D. Cimino

(57) ABSTRACT

A method of forming a drug delivery device includes laser forming a top ceramic plate to include an inner portion including top laser micromachined through-holes while not lasering a planar outer portion. Top nanochannels are formed into the top ceramic plate to provide fluid connections between neighboring to micromachined through-holes. A bottom ceramic plate is laser formed to include an inner portion including bottom laser micromachined through-holes while not lasering a planar outer portion. Bottom nanochannels are formed into the bottom ceramic plate to provide fluid connections between neighboring to micromachined through-holes. A bonding material is applied to the planar outer portion of the top and/or bottom ceramic plate. The top and bottom ceramic plate are aligned so that the top and bottom laser micromachined through-holes are laterally offset from one another. The top ceramic plate is bonded to the bottom ceramic plate with a bonding material.

13 Claims, 4 Drawing Sheets

CERAMIC NANOCHANNEL DRUG DELIVERY DEVICE AND METHOD OF FORMATION

FIELD

Disclosed embodiments relate to drug delivery flow devices having nanochannels for restricting the rate of release of a drug stored in reservoir, typically defined by a capsule.

BACKGROUND

Drug delivery can be provided by silicon-based multilayered drug delivery flow devices fabricated using a conventional microfabrication process, such as to produce a nanopore membrane for continuous passive drug release to maintain a constant drug concentration in a patient's bloodstream throughout the delivery period. Based on known silicon microfabrication technology, including photolithography and reactive ion etching (RIE), the dimensions of the nanochannel areas, as well as microchannel areas, can be well controlled, thus providing a steady, constant drug release rate over an extended time period. These known multilayered nanochannel structures extend the limit of release rate range over a single-layer nanochannel system, and allow a wide range of pre-defined porosity to achieve essentially any desired drug release rate using any desired nanochannel size. The nanochannel length can generally be reduced to the nanofabrication limit of the process, i.e., 10 s of nms.

A conventional nanochannel drug delivery system membrane comprises a sandwich including a thin top layer, horizontal nanochannels, and a thicker bottom wafer (or chip). The nanochannel thickness controls the rate of drug release. The thin top layer houses an array of nanochannels that provides the inlet port for diffusing drug molecules. The top layer functions as a lid for the nanochannels by providing the nanochannels a top surface. The nanochannels may be fabricated by a sacrificial layer technique to obtain smooth surfaces and well controlled dimensions.

Issues with materials inside the human body include rejection by the body, causing basically an infection, where the material acts as a foreign agent. A second issue arises when the body can dissolve the material. One problem with conventional silicon-based drug-delivery devices is that silicon tends to dissolve in the body, and thus can lead to adverse effects. Silicon-based drug delivery devices must thus generally be protected (coated) by body-friendly non-silicon layers such as silicon nitride or tungsten, which adds steps to the process and raises the cost of the device.

SUMMARY

This Summary is provided to introduce a brief selection of disclosed concepts in a simplified form that are further described below in the Detailed Description including the drawings provided. This Summary is not intended to limit the claimed subject matter's scope.

Disclosed embodiments describe ceramic drug delivery devices that may be formed using conventional integrated circuit (IC) fabrication techniques. An example method of forming a drug delivery device includes laser forming a top ceramic (e.g., alumina, which is a body friendly ceramic material) plate to include an inner portion including top laser micromachined through-holes, while not lasering a planar outer portion. Disclosed laser micromachined through-holes as known in the laser arts are structurally unique having a distinct rounding at the top surface corresponding to laser beam entrance, a substantially smooth sidewall surface, and a slight taper so that the bottom is slightly narrower than the top of the through-hole. This through-hole structure can be compared to conventional deep reactive ion etched (RIE) through-holes which lack rounding at the top surface, and have jagged sidewalls protruding 10 nm or 100 s of nms (or more) relative to trough regions of the sidewall due to alternating the RIE etch between two different etch gases.

Top nanochannels are formed into the top ceramic plate to provide fluid connections between neighboring top laser micromachined through-holes. A bottom ceramic plate is laser formed to include an inner portion including bottom laser micromachined through-holes while not lasering a planar outer portion. Bottom nanochannels are formed into the bottom ceramic plate to provide fluid connections between neighboring bottom laser micromachined through-holes.

A bonding material is applied to the planar outer portion of the top and/or bottom ceramic plate. The top and bottom ceramic plate are aligned so that the top and bottom laser micromachined through-holes are laterally offset from one another. The top ceramic plate is then bonded to the bottom ceramic plate with the bonding material.

BRIEF DESCRIPTION OF THE DRAWINGS

Reference will now be made to the accompanying drawings, which are not necessarily drawn to scale, wherein.

DETAILED DESCRIPTION

Figure 1A:
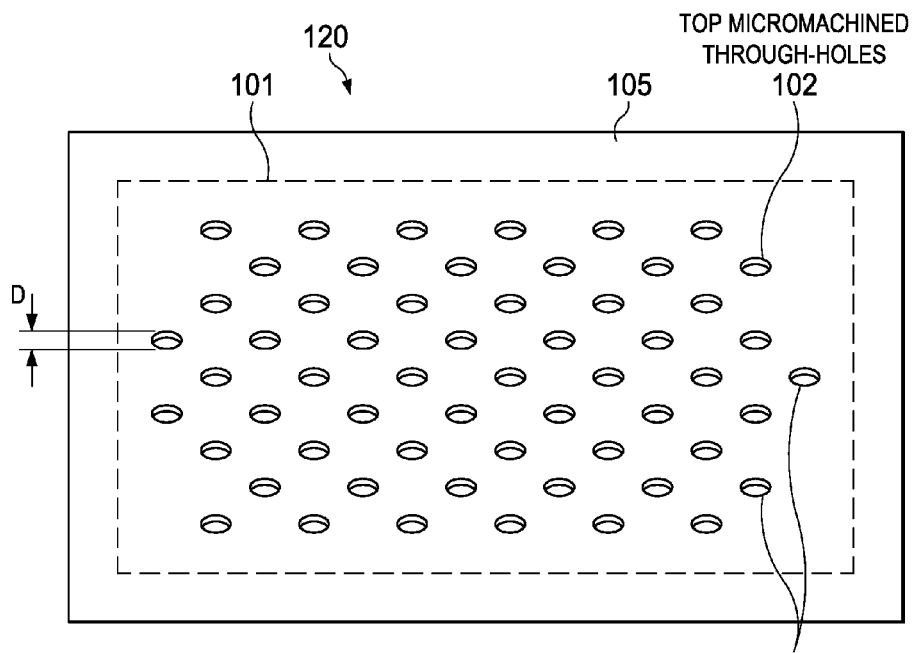
FIG. 1A depicts a ceramic top plate having an inner portion including a plurality of top laser micro-machined through-holes and a planar (without holes) outer portion, according to an example embodiment.

Example embodiments are described with reference to the drawings, wherein like reference numerals are used to designate similar or equivalent elements. Illustrated ordering of acts or events should not be considered as limiting, as some acts or events may occur in different order and/or concurrently with other acts or events. Furthermore, some illustrated acts or events may not be required to implement a methodology in accordance with this disclosure.

FIG. 1A depicts a ceramic top plate 120 having an inner portion 101 including a plurality of top laser micro-machined through-holes 102 and a planar (without micro-machined holes) outer portion 105, according to an example embodiment. Disclosed plates such as ceramic top plate 120 are generally processed in wafer form having several thousand or more die each providing a ceramic plate. Such wafers generally being processed in semiconductor clean room facilities minimize dust accumulation, and for some embodiments utilize photolithography and etch equipment therein. Die dimensions (after wafer singulation) may be in the range of several mms on each side, such as 6 mm by 10 mm in one particular embodiment, yielding thousands of die for 300 mm wafers, for example.

In one embodiment the ceramic material comprises alumina. Other ceramic materials may also be used, such as, but not limited to, zirconia ($ZrO_2$), silicon carbide (SiC), or other body friendly ceramics.

The top laser micro-machined through-holes 102 are shown being essentially circular in cross-section, having a diameter shown as D. D is generally for 300 nm to 3 µm, such as 1 µm in one particular embodiment. Although shown as having a circular cross-section, disclosed laser micro-machined through-holes may have a variety of other shapes, such as oval, square or rectangular. A programmable laser system (e.g., a $CO_2$ laser system) with a positioning scanner can be used for the lasering. Such a programmable laser system may already be used in the wafer fab facility for singulating wafers after wafer probe into die.

Programmed laser parameters can include position, laser sweep speed, frequency (through choice of laser), time and power, which contribute to control of the depth of the laser etch. Disclosed layer processing will generally include a laser residue clean-up process such as a Chemical Mechanical Polish (CMP) or variations thereof to remove laser residue generated by forming the top laser micro-machined through-holes 102 falling on the ceramic top plate 120 during laser processing to maintain a high level of planarity provided by the incoming ceramic substrates (e.g., alumina wafers).

As described below, a laser system may also be used to form the nanochannels which fluidicly connect neighboring laser micro-machined through-holes, such as top laser micro-machined through-holes 102. In the case of laser formed nanochannels, more than one depth and width can be programmed to be provided on the same ceramic plate, such 5 nm in the x-direction and 3 nm in the y-direction.

Figure 1B:
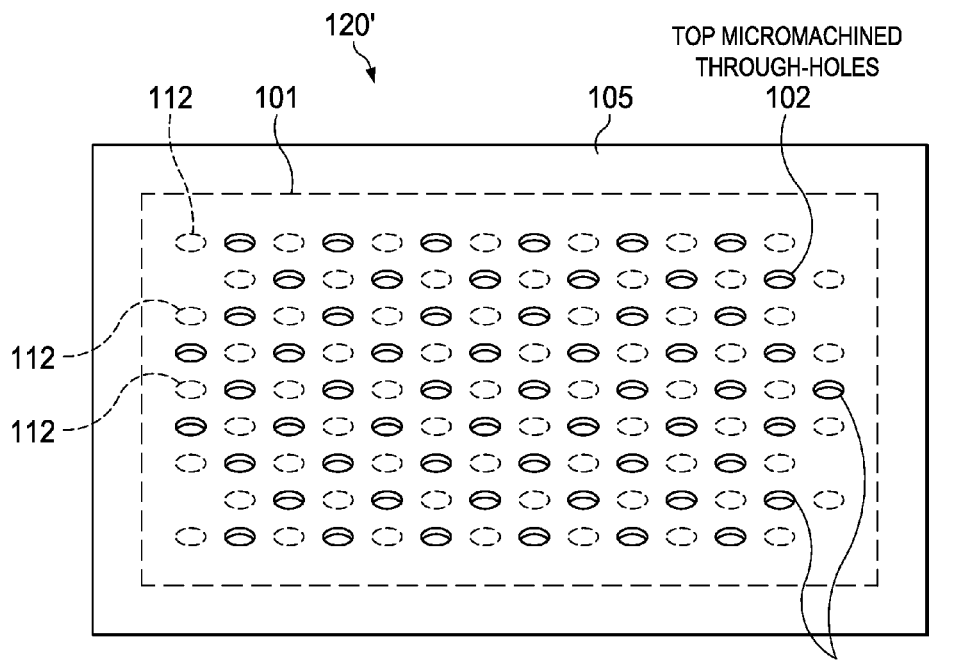
FIG. 1B depicts the ceramic top plate with the laser micromachined through-holes in FIG. 1A along with a representation of the locations of laser micro-machined through-holes of the bottom plate, according to an example embodiment.

FIG. 1B depicts the ceramic top plate 120' with the top laser micro-machined holes 102 in FIG. 1A along with a dashed-line representation of the locations of bottom laser micro-machined through-holes 112 that are on the bottom ceramic plate according to an example embodiment. Note the lateral offset in laser micro-machined hole position between the top laser micro-machined holes 102 in the ceramic top plate and the bottom laser micro-machined holes 112 in the ceramic bottom plate.

Figure 2:
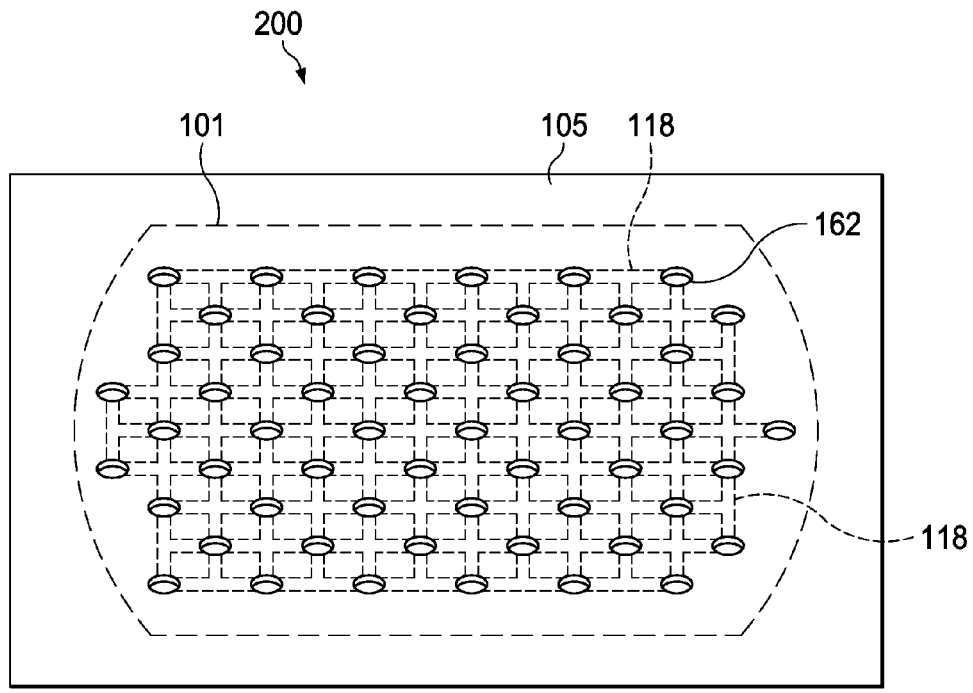
FIG. 2 depicts a ceramic plate with laser micro-machined through-holes and etched nanochannels connecting neighboring laser micro-machined through-holes, according to an example embodiment.

FIG. 2 depicts a ceramic plate 200 with laser micro-machined through-holes shown as 162 and nanochannels 118 running in two directions (e.g., x and y) connecting neighboring ones of the laser micro-machined through-holes 162, according to an example embodiment. Ceramic plate 200 may be used as a top ceramic plate or a bottom ceramic plate. The depth of the nanochannels 118 used will generally dependent on the size of the molecule of the particular drug to be dispensed, with larger sized nanochannels 118 in both the width and depth dimension for larger drug molecules and smaller sized nanochannels 118 in both the width and depth dimension for smaller drug molecules. Nanochannels 118 may be formed in a variety of sizes, with typical depths being 3 nm to 50 nm and typical widths being 0.5 µm to 2.0 µm. As noted above, more than one width and depth can be provided on a given ceramic plate (e.g., 5 nm in the x-direction and 3 nm in the y-direction).

Figure 3:
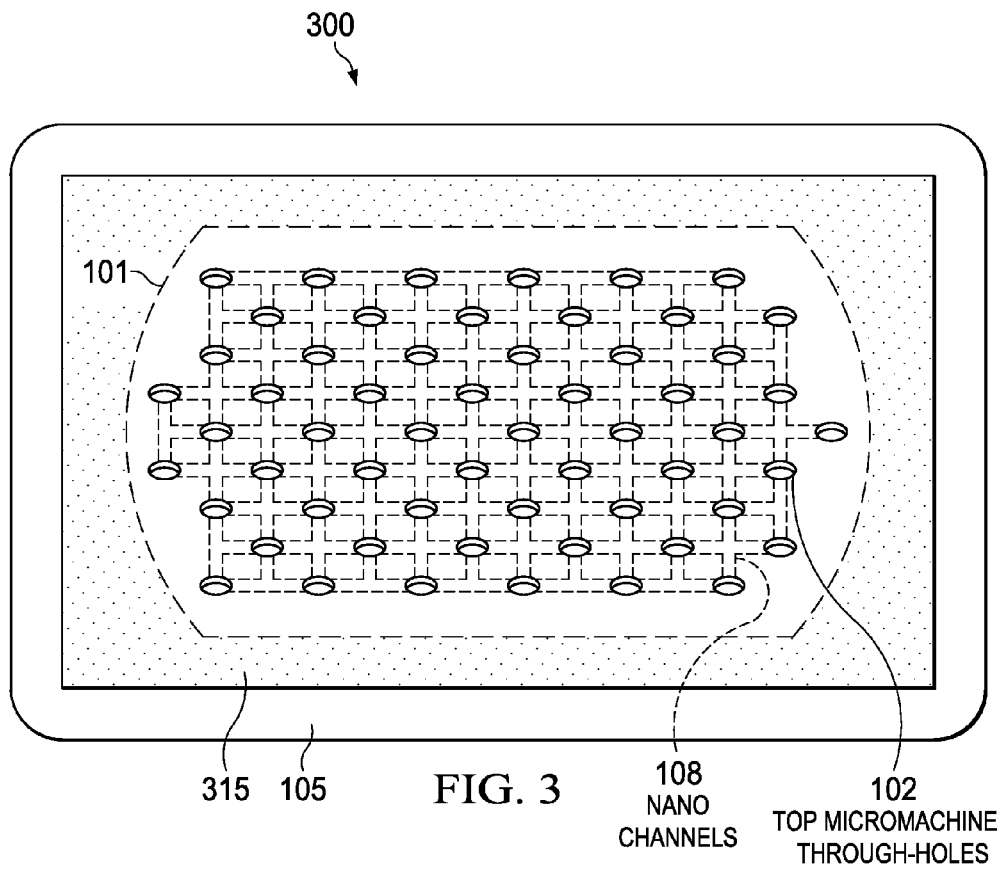
FIG. 3 depicts a ceramic plate with laser micro-machined through-holes including a patterned bonding material on the outer portion defining a bonding area, according to an example embodiment.

FIG. 3 depicts a top ceramic plate 300 with top laser micromachined through-holes 102 including a patterned bonding material 315 on a portion of the outer portion 105 that as shown borders the periphery of the inner portion 101, according to an example embodiment. In one embodiment the patterned bonding material 315 comprises a metal material that is a body friendly metal, such as gold (Au). In another embodiment the metal material comprises tungsten (W). In yet another embodiment the patterned bonding material 315 comprises a ceramic frit which is a ceramic composition subjected to a special fusing oven, quenched to form a glass, and then granulated into a powdery form. Conventional lithography and etch can be used to provide the patterned bonding material 315 shown in FIG. 3. The patterned bonding material 315 is generally 1 nm to 10 nm thick, but can be thicker or thinner than this range, but is typically thinner than the depth of the nanochannels 118.

Figure 4:
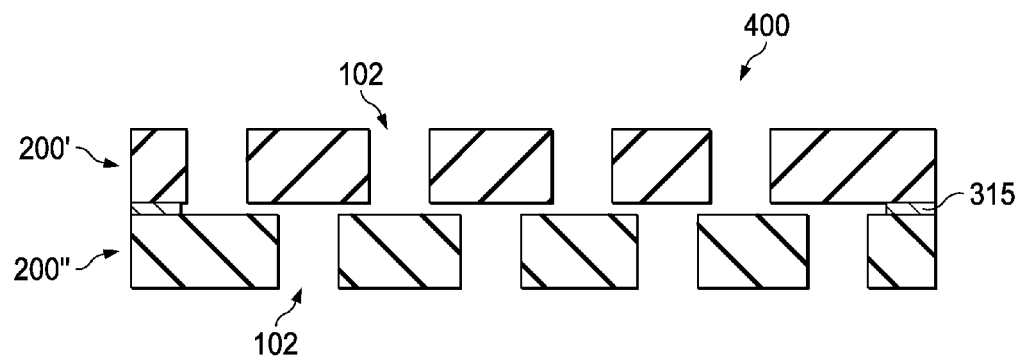
FIG. 4 is a cross sectional depiction of an example drug delivery device including top and bottom ceramic plates spaced apart by a bonding material, according to an example embodiment.

FIG. 4 is a cross sectional depiction of an example drug delivery device 400 including a top ceramic plate 200' and bottom ceramic plate 200" spaced apart and secured together by the patterned bonding material 315 which provides a bonding area/region, according to an example embodiment. Depending on flow rate and amount of drug to be delivered, drug delivery device 400 will typically be 20 mm to 50 mm on a side with a typical height or thickness of 1 mm to 2 mm. The nanochannels 118 connecting the neighboring top laser micro-machined through-holes 102 in the top ceramic plate 200' and neighboring bottom laser micro-machined through-holes 112 in the bottom ceramic plate 200" are not shown in the cross-sectional depiction provided. The thickness of the patterned bonding material 315 can be seen to define the spacing between the ceramic plates 200' and 200", and may be used as a device design parameter in conjunction with the nanochannels 118 to define the rate of drug release from a drug reservoir (see implantable capsule 500 shown in FIG. 5 described below).

Figure 5:
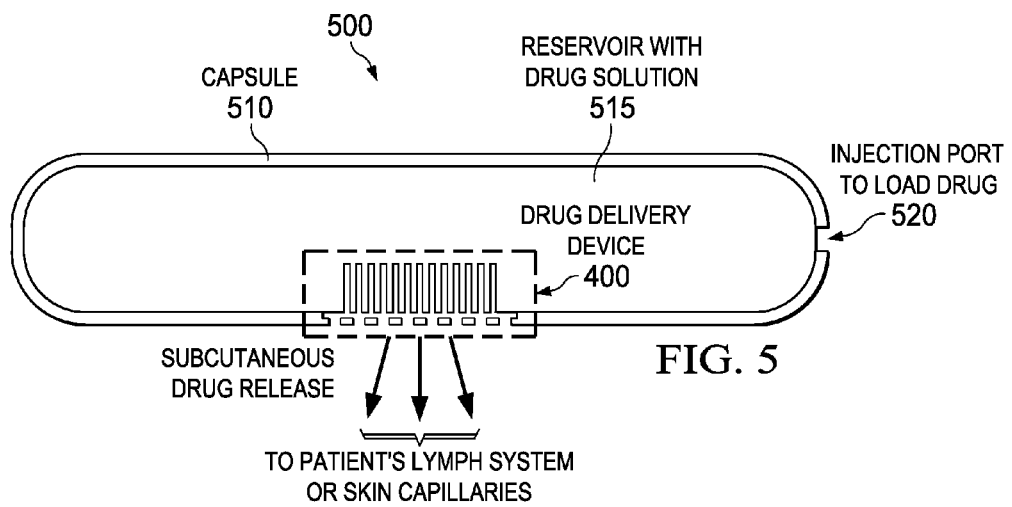
FIG. 5 depicts an implantable capsule including a disclosed drug delivery device, according to an example embodiment.

FIG. 5 depicts an implantable capsule 500 including the drug delivery device 400 depicted in FIG. 4, according to an example embodiment. Implantable capsule 500 includes an outer capsule 510 (e.g., rubber) for implantation into the body of a patient which defines an inner reservoir 515 having a drug solution therein, and an injection port 520 for loading a drug into the capsule 510. The implantable capsule 500 has an opening in which the drug delivery device is generally pressed into U shaped indentations molded into the capsule opening. Once implantable capsule 500 is subcutaneously implanted into the body of the patient, the drug from within the implantable capsule 500 is slowly released by the drug delivery device 400, at a rate primarily determined by the thickness of the bonding material which defines the plate separation distance, where the drug once released is then picked up by the lymph system and/or skin capillaries of the patient.

Figure 6:
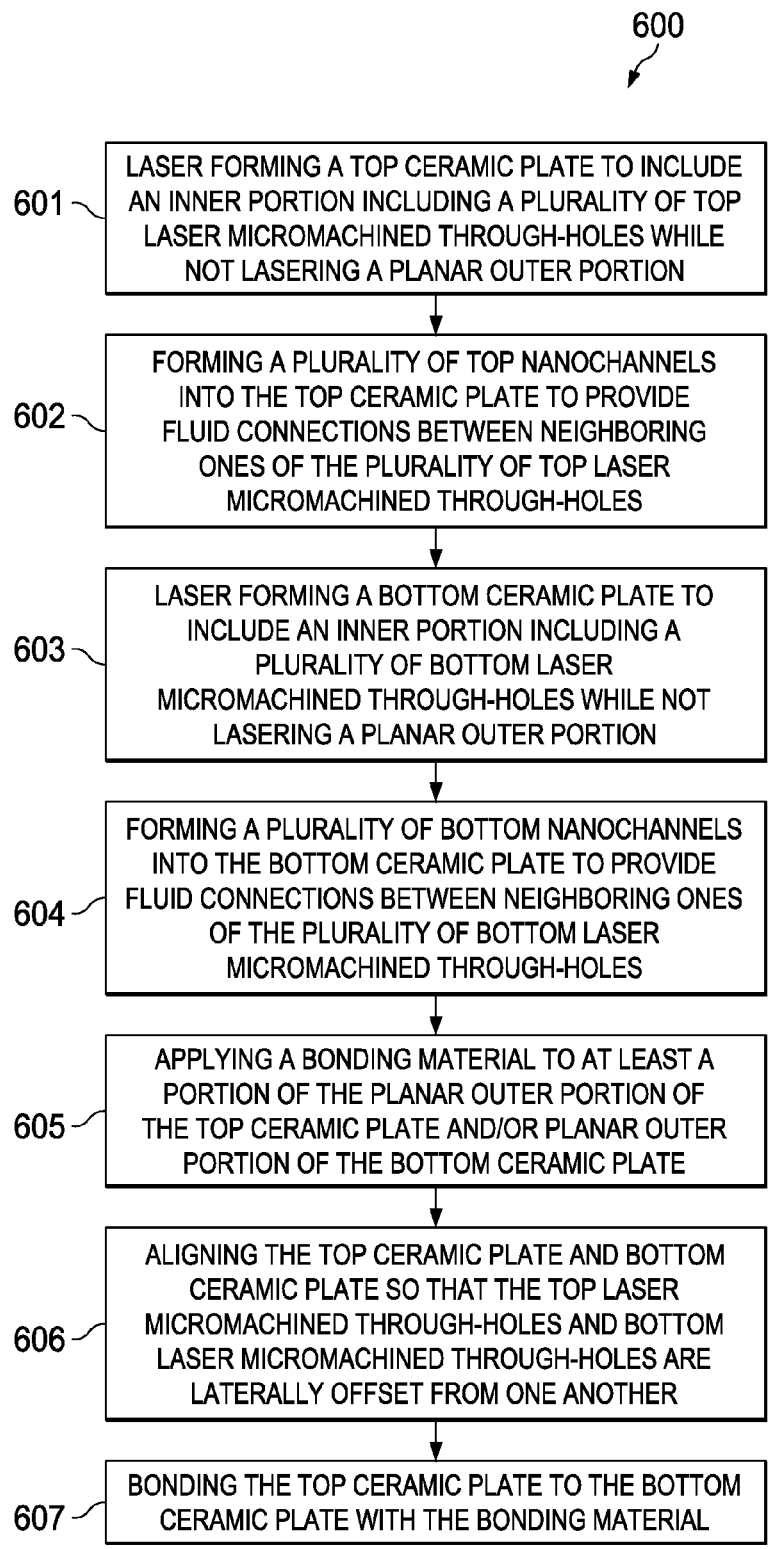
FIG. 6 is a flow chart that shows steps in an example method of forming a drug delivery device, according to an example embodiment.

FIG. 6 is a flow chart that shows steps in an example method 600 of forming a drug delivery device, according to an example embodiment. Step 601 comprises laser forming a top ceramic plate to include an inner portion including a plurality of top laser micromachined through-holes while not lasering a planar outer portion. Step 602 comprises forming a plurality of top nanochannels into the top ceramic plate to provide fluid connections between neighboring ones of the plurality of top laser micromachined through-holes. Step 603 comprises laser forming a bottom ceramic plate to include an inner portion including a plurality of bottom laser micromachined through-holes while not lasering a planar outer portion. Step 604 comprises forming a plurality of bottom nanochannels into the bottom ceramic plate to provide fluid connections between neighboring ones of the plurality of bottom laser micromachined through-holes.

Step 605 comprises applying a bonding material to at least a portion of the planar outer portion of the top ceramic plate and/or planar outer portion of said bottom ceramic plate. Step 606 comprises aligning the top ceramic plate and bottom ceramic plate so that the top laser micromachined through-holes and bottom laser micromachined through-holes are laterally offset from one another (such as depicted in FIG. 4). The alignment process is performed at the substrate (e.g., wafer) level, such as by having the wafer's flats aligned. This will align all the individual drug delivery devices which can later be separated, such as by a typical diamond saw process. Step 607 comprises bonding the top ceramic plate to the bottom ceramic plate with the bonding material. The bonding process generally comprises a pressure and heating process, such as used in typical semiconductor wafer bonding processes. A singulation process then generally follows to separate the drug delivery device 400 bonded stacked die from one another. Singulation of the drug delivery devices can be accomplished by a diamond saw as used in conventional semiconductor die singulation processes.

Advantages of disclosed embodiments include being clean room friendly, high volume manufacturable (e.g., fabricated in wafer form), relatively easy to test, and low cost. One method to test disclosed drug delivery devices uses krypton-85 gas flow techniques, where devices are placed under krypton-85 gas pressure and a radioactive count is measured. Disclosed drug delivery devices are body friendly being formed from non-dissolving and non-toxic ceramic materials. Disclosed drug delivery devices also provide minimal cell growth clogging, high fracturing strength, and essentially no time-dependant effects due to stresses one implanted in the patient.

Those skilled in the art to which this disclosure relates will appreciate that many other embodiments and variations of embodiments are possible within the scope of the claimed invention, and further additions, deletions, substitutions and modifications may be made to the described embodiments without departing from the scope of this disclosure.

The invention claimed is:

1. A method of forming a drug delivery device, comprising:
    laser forming a top ceramic plate to include an inner portion including a plurality of top laser micromachined through-holes while not lasering a planar outer portion;
    forming a plurality of top nanochannels into said top ceramic plate to provide fluid connections between neighboring ones of said plurality of top laser micromachined through-holes;
    laser forming a bottom ceramic plate to include an inner portion including a plurality of bottom laser micromachined through-holes while not lasering a planar outer portion;
    forming a plurality of bottom nanochannels into said bottom ceramic plate to provide fluid connections between neighboring ones of said plurality of bottom laser micromachined through-holes;
    applying a bonding material to at least a portion of said planar outer portion of said top ceramic plate and/or said planar outer portion of said bottom ceramic plate;
    aligning said top ceramic plate and said bottom ceramic plate so that said plurality of top laser micromachined through-holes and said plurality of bottom laser micromachined through-holes are laterally offset from one another; and
    bonding said top ceramic plate to said bottom ceramic plate with said bonding material.

2. The method of claim 1, wherein said forming said plurality of top nanochannels and said forming said plurality of bottom nanochannels both comprise laser forming.

3. The method of claim 1, wherein said forming said plurality of top nanochannels and said forming said plurality of bottom nanochannels both comprise, before said bonding, depositing said bonding material, patterning said bonding material, and etching said bonding material.

4. The method of claim 1, wherein said bonding material comprises a metal.

5. The method of claim 4, wherein said metal comprises tungsten (W) or gold (Au).

6. The method of claim 1, wherein said bonding material comprises glass frit.

7. The method of claim 1, wherein said top ceramic plate and said bottom ceramic plate both comprise alumina.

8. The method of claim 1, wherein a thickness of said bonding material is from 1 nm to 10 nm.

9. A drug delivery device, comprising:
    a top ceramic plate including an inner portion including a plurality of top laser micromachined through-holes and a planar outer portion and a plurality of top nanochannels into said top ceramic plate that provide fluid connections between neighboring ones of said plurality of top laser micromachined through-holes;
    a bottom ceramic plate including an inner portion including a plurality of bottom laser micromachined through-holes and a planar outer portion and a plurality of bottom nanochannels into said bottom ceramic plate that provide fluid connections between neighboring ones of said plurality of bottom laser micromachined through-holes;
    a bonding material on at least a portion between said planar outer portion of said top ceramic plate and/or said planar outer portion of said bottom ceramic plate;
    wherein said top ceramic plate and said bottom ceramic plate are aligned to one another so that said plurality of top laser micromachined through-holes and said plurality of bottom laser micromachined through-holes are laterally offset from one another.

10. The drug delivery device of claim 9, wherein said bonding material comprises a metal.

11. The drug delivery device of claim 10, wherein said metal comprises tungsten (W) or gold (Au).

12. The drug delivery device of claim 9, wherein said bonding material comprises glass frit.

13. The drug delivery device of claim 9, wherein said top ceramic plate and said bottom ceramic plate both comprise alumina.

* * * * *